(12) United States Patent
Schurman (10) Patent No.: US 7,356,365 B2
(45) Date of Patent: Apr. 8, 2008

(54) METHOD AND APPARATUS FOR TISSUE OXIMETRY

(75) Inventor: Matthew J. Schurman, Somerset, NJ (US)

(73) Assignee: GlucoLight Corporation, Bethlehem, PA (US)

( * ) Notice: Subject to any disclaimer, the term of this patent is extended or adjusted under 35 U.S.C. 154(b) by 180 days.

(21) Appl. No.: 10/884,298

(22) Filed: Jul. 2, 2004

(65) Prior Publication Data

US 2005/0059868 A1   Mar. 17, 2005

Related U.S. Application Data

(60) Provisional application No. 60/485,761, filed on Jul. 9, 2003.

(51) Int. Cl.
*A61B 5/1455* (2006.01)

(52) U.S. Cl. .................................... 600/323

(58) Field of Classification Search ............... 600/323, 600/328, 334, 310, 322
See application file for complete search history.

(56) References Cited

U.S. PATENT DOCUMENTS

| | | | |
|---|---|---|---|
| 3,826,905 A | 7/1974 | Valkama et al. | 235/151.12 |
| 3,958,560 A | 5/1976 | March | 128/2 A |
| 4,014,321 A | 3/1977 | March | 128/2 A |
| 4,476,875 A | 10/1984 | Nilsson et al. | 128/666 |
| 4,590,948 A | 5/1986 | Nilsson | 128/666 |
| 4,606,351 A | 8/1986 | Lüubbers | 128/633 |
| 4,655,225 A | 4/1987 | Dähne et al. | 128/633 |
| 4,704,029 A | 11/1987 | Van Heuvelen | 356/39 |
| 4,750,830 A | 6/1988 | Lee | 351/211 |
| 4,832,035 A * | 5/1989 | Cho et al. | 600/328 |
| 4,834,111 A | 5/1989 | Khanna et al. | 128/774 |
| 4,873,989 A | 10/1989 | Einzig | 128/692 |
| 4,882,492 A | 11/1989 | Schlager | 250/346 |
| 4,883,953 A | 11/1989 | Koashi et al. | 250/226 |
| 4,890,621 A | 1/1990 | Hakky | 128/635 |

(Continued)

FOREIGN PATENT DOCUMENTS

EP        0282234        9/1988

(Continued)

OTHER PUBLICATIONS

Arnold, M.A., et al, "Determination of Physiological Levels of Glucose in an Aqueous Matrix with Digitally Filtered Fourier Transform Near-Infrared Spectra," Anal. Chem., vol. 64, No. 14, pp. 1457-1464 (1990).

(Continued)

*Primary Examiner*—Eric F Winakur
(74) *Attorney, Agent, or Firm*—Thomas J. Engellenner; Charlton Shen; Nutter McClennen & Fish LLP (57) ABSTRACT

In accordance with the invention, the oxygenation of blood-profused tissue is measured by shining light into the profused tissue and analyzing the light reflected within the tissue. The light is reflected by cell walls in the tissue and is partially absorbed by hemoglobin in the blood. Since the extent of absorption is sensitive to the extent of hemoglobin oxygenation, measurement and processing of the reflected light provides a measure of the oxygenation of the blood. In one embodiment, the method is applied to measure the oxygenation of blood within the tympanic membrane (ear drum).

12 Claims, 4 Drawing Sheets

U.S. PATENT DOCUMENTS

| | | | |
|---|---|---|---|
| 4,901,728 A | 2/1990 | Hutchison | 128/633 |
| 4,948,248 A | 8/1990 | Lehman | 356/40 |
| 4,979,509 A | 12/1990 | Hakky | 128/635 |
| 4,989,978 A | 2/1991 | Groner | 356/343 |
| 5,025,785 A | 6/1991 | Weiss | 128/633 |
| 5,028,787 A | 7/1991 | Rosenthal et al. | 250/341 |
| 5,054,487 A | 10/1991 | Clarke | 128/633 |
| 5,070,874 A | 12/1991 | Barnes et al. | 128/633 |
| 5,101,814 A | 4/1992 | Palti | 128/635 |
| 5,112,124 A | 5/1992 | Harjunmaa et al. | 356/39 |
| 5,115,133 A | 5/1992 | Knudson | 250/341 |
| 5,168,325 A | 12/1992 | Yoder-Short | 356/361 |
| 5,178,153 A | 1/1993 | Einzig | 128/692 |
| 5,209,231 A | 5/1993 | Cote et al. | 128/633 |
| 5,222,495 A | 6/1993 | Clarke et al. | 128/633 |
| 5,222,496 A | 6/1993 | Clarke et al. | 128/633 |
| 5,243,983 A | 9/1993 | Tarr et al. | 128/633 |
| 5,267,152 A | 11/1993 | Yang et al. | 364/413.09 |
| 5,277,181 A | 1/1994 | Mendelson et al. | 128/633 |
| 5,313,941 A | 5/1994 | Braig et al. | 128/633 |
| 5,321,501 A | 6/1994 | Swanson et al. | 356/345 |
| 5,341,805 A | 8/1994 | Stavridi et al. | 128/633 |
| 5,348,003 A | 9/1994 | Caro | 128/633 |
| 5,349,953 A | 9/1994 | McCarthy et al. | 128/633 |
| 5,361,758 A | 11/1994 | Hall et al. | 128/633 |
| 5,370,114 A | 12/1994 | Wong et al. | 128/633 |
| 5,376,336 A | 12/1994 | Lübbers et al. | 422/82.06 |
| 5,379,238 A | 1/1995 | Stark | 364/578 |
| 5,383,452 A | 1/1995 | Buchert | 128/633 |
| 5,398,681 A | 3/1995 | Kupershmidt | 128/633 |
| 5,433,197 A | 7/1995 | Stark | 128/633 |
| 5,435,309 A | 7/1995 | Thomas et al. | 128/633 |
| 5,448,992 A | 9/1995 | Kupershmidt | 128/633 |
| 5,452,716 A | 9/1995 | Clift | 128/633 |
| 5,457,535 A | 10/1995 | Schmidtke et al. | 356/364 |
| 5,459,570 A | 10/1995 | Swanson et al. | 356/345 |
| 5,492,118 A | 2/1996 | Gratton et al. | 128/633 |
| 5,501,226 A | 3/1996 | Petersen et al. | 128/691 |
| 5,535,743 A | 7/1996 | Backhaus et al. | 128/633 |
| 5,549,114 A | 8/1996 | Petersen et al. | 128/691 |
| 5,551,422 A | 9/1996 | Simonsen et al. | 128/633 |
| 5,553,616 A | 9/1996 | Ham et al. | 128/633 |
| 5,582,168 A | 12/1996 | Samuels et al. | 128/633 |
| 5,601,087 A * | 2/1997 | Gunderson et al. | 600/473 |
| 5,710,630 A | 1/1998 | Essenpreis et al. | 356/345 |
| 5,795,295 A | 8/1998 | Hellmuth et al. | 600/407 |
| 6,430,513 B1 * | 8/2002 | Wang et al. | 702/28 |
| 6,443,881 B1 | 9/2002 | Finger | 600/1 |
| 6,556,853 B1 | 4/2003 | Cabib et al. | 600/407 |
| 6,725,073 B1 * | 4/2004 | Motamedi et al. | 600/316 |
| 6,837,337 B2 | 1/2005 | Thomas et al. | 182/8 |
| 6,847,449 B2 * | 1/2005 | Bashkansky et al. | 356/364 |
| 2002/0016533 A1 | 2/2002 | Marchitto et al. | 600/310 |
| 2003/0107742 A1* | 6/2003 | Tualle | 356/450 |
| 2003/0137669 A1* | 7/2003 | Rollins et al. | 356/479 |

FOREIGN PATENT DOCUMENTS

| | | |
|---|---|---|
| EP | 0160768 | 5/1989 |
| EP | 0127947 | 8/1990 |
| EP | 0280986 | 7/1992 |
| EP | 0317121 | 2/1994 |
| EP | 0536187 | 9/1994 |
| EP | 0589191 | 3/1997 |
| EP | 0603658 | 2/1999 |
| EP | 0631137 | 3/2002 |
| EP | 0670143 | 5/2003 |
| WO | WO 88/06726 | 9/1988 |
| WO | WO 89/10087 | 11/1989 |
| WO | WO 91/18548 | 12/1991 |
| WO | WO 92/10131 | 6/1992 |
| WO | WO 92/17765 | 10/1992 |
| WO | WO 93/00855 | 1/1993 |
| WO | WO 93/07801 | 4/1993 |
| WO | WO 93/09421 | 5/1993 |
| WO | WO 93/16629 | 9/1993 |
| WO | WO 94/04070 | 3/1994 |
| WO | WO 94/13193 | 6/1994 |
| WO | WO 95/32416 | 11/1995 |

OTHER PUBLICATIONS

Arnold, V.W., "Fourier transformation infrared spectrometry—a new (old) method of detection in forensic chemistry and criminal investigation," Beitr Gerichtl Med., vol. 47, pp. 123-147 (1989).

Bruulsema, J. T., "Correlation between blood glucose concentration in diabetics and nonivasively measured tissue optical scattering coefficient," Opt. Lett., vol. 22, No. 3, pp. 190-193 (1997).

Burritt, M.F., "Current analytical approaches to measuring blood analytes," Clin. Chem., vol. 36, No. 8 Pt. 2, pp. 1562-1566 (1990).

Chira, I.S. et al, "Light scaterring by blood components after supplying glucose," Biomed. Tech., vol. 35, No. 5, pp. 102-106 (1990).

Christison, G.B., et al, "Laser photoacoustic determination of physiological glucose concentrations in human whole blood," Med. Biol. Eng. Comput., vol. 31, No. 3, pp. 284-290 (1993).

Cote, G. L., et al, "Noninvasive optical polarimetric glucose sensing using a true phase measurement technique," IEEE Trans. Biomed. Eng., vol. 39, No. 7, pp. 752-756 (1992).

Drezek, R., et al, "Light scattering from cell: finite-difference time-domain simulations and goniometric measurements," Appl. Opt., vol. 38, No. 16, pp. 3651-3661 (1999).

Duck, F. A., Physical Properties of Tissue, (Academic London 1990).

Dyer, D. G., et al, "Accumulation of Maillard Reaction Products in Skin Collagen in Diabetes and Aging," J. Clin. Invest., vol. 91, pp. 2463-2469 (1993).

Esenaliev, R. O., et al, "Noninvasive monitoring of glucose concentration with optical coherence tomography," Optics Letters, vol. 26, No. 13, pp. 992-994 (Jul. 1, 2001).

Faber, D. J., et al, "Light absorption of (oxy-) hemoglobin assessed by spectroscopic optical coherence tomography," Optics Letters, vol. 28, No. 16, pp. 1436-1438 (Aug. 15, 2003).

Fercher, A., et al, "In vivo optical coherence tomography," Amer. J. Opthalmol., vol. 116, No. 1, pp. 113-114 (1993).

Flock, S.T., et al, "Total attenuation coeffecients and scattering phase functions of tissues and phantom materials at 633 nm," Med. Phys., vol. 14, No. 5, pp. 835-841 (1987).

Fogt, E.J., "Continuous ex vivo and in vivo monitoring with chemical sensors," Clin. Chem., vol. 36, No. 8 Pt. 2, pp. 1573-1580 (1990).

Frank, K.H., et al, "Measurements of angular distributions of Rayleigh and Mie scattering events in biological models," Phys. Med. Biol., vol. 34, No. 8, pp. 1901-1916 (1989).

Gabriely, I., et al, "Transcutaneous glucose measurement using near-infrared spectroscopy during hypoglycemia," Diabetes Care, vol. 22, No. 12, pp. 2026-2032 (1999).

Galanzha, E. I., et al, "Skin backreflectance and microvascular system functioning at the action of osomtic agents," J. Phys. D. Appl. Phys., vol. 36, pp. 1739-1746 (2003).

Gilbert, J.W., et al, "A cerebrospinal fluid glucose biosensor for diabetes mellitus," ASAIO J., vol. 38, No. 2, pp. 82-87 (1992).

Goetz Jr., M. J., et al, "Application of a multivariate technique to Raman spectra for quantification of body chemicals," IEEE Trans. Biomed. Eng., vol. 42, pp. 728-731 (1995).

Goodman, J. W., "Some fundamental properties of speckle," Journal of the Optical Society of America, vol. 66, No. 11, pp. 1145-1150 (Nov. 1976).

Gough, D.A., "The composition and optical rotary dispersion of bovine aqueous humor," Diabetes Care, vol. 5, No. 3, pp. 266-270 (May-Jun. 1982).

Gunby, P., "Laser-implant contact lens could be glucose monitor," JAMA, vol. 243, No. 4, pp. 317 (1980).

Guton, A.C., Textbook of medical physiology, (W.B. Saunders Company 1992).

Huang, D., et al., "Optical Coherence Tomography," Science, vol. 254, pp. 1178-1181 (1991).

Huang, Y.L., et al, "On-line determination of glucose concentration throughout animal cell cultures based on chemiluminescent detection of hydrogen peroxide coupled with flow-injection analysis," J. Biotechnol., vol. 18, No. 1-2, pp. 161-172 (1991).

Kaiser, N., "Laser absorption spectroscopy with an ATR prism —noninvasive in vivo determination of glucose," Horm. Metab. Res. Suppl., vol. 8, pp. 30-33 (1979).

Kajiwara, K., et al, "Spectroscopic quantitative analysis of blood glucose by Fourier transform infrared spectroscopy with an attenuated total reflection prism," Med. Prog. Technol., vol. 18, No. 3, pp. 181-189 (1992).

Khalil, O. S., "Spectroscopic and clinical aspects of noninvasive glucose measurements," Clinical Chemistry, vol. 45, No. 2, pp. 165-177 (1999).

Kholodnykh, A. I., et al, "Precision of measurement of tissue optical properties with optical coherence tomography," Applied Optics, vol. 42, No. 16, pp. 3027-3037 (Jun. 1, 2003).

King, T. W., et al, "Multispectral polarimetric glucose detection using a single pockels cell," Optical Engineering, vol. 33 No. 8, pp. 2746-2753 (1994).

Kohl, M., et al, "Influence of glucose concentration on light scattering in tissue-simulating phamtoms ," Optics Letters, vol. 19, No. 24, pp. 2170-2172 (Dec. 15, 1994).

Kohl, M., et al, "The influence of glucose concentration upon the transport of light in tissue-simulating phantoms," Phys. Med. Biol., vol. 40, pp. 1267-1287 (1995).

Kruse-Jarres, J.D., "Physiocochemical determinations of glucose in vivo," J. Clin. Chem. Clin. Biochem., vol. 26, No. 4, pp. 201-208 (1988).

Larin, K. V., et al, "Optoacoustic signal profiles for monitoring glucose concentration in turbid media," SPIE Proc., vol. 3726, pp. 576-583 (1988).

Larin, K. V., et al, "Noninvasive Blood Glucose Monitoring with Optical Coherence Tomography," Diabetes Care, vol. 25, No. 12, pp. 2263-2267 (Dec. 2002).

Larin, K. V., et al, "Specificity of noninvasive blood glucose sensing using optical coherence tomography technique: a pilot study," Physics in Medicine and Biology, vol. 48, pp. 1371-1390 (2003).

Larin, K. V., et al, "Phase-sensitive optical low-coherence reflectometry for the detection of analyte concentrations," Applied Optics, vol. 43, No. 17, pp. 3408-3414 (Jun. 10, 2004).

Lide, D.R., CRC Handbook of Chemistry and Physics, 79th ed. (CRC Press, Boca Raton, Florida, 1998).

MacKenzie, H. A., et al, "Advances in photoacoustic noninvasive glucose testing," Clin. Chem., vol. 45, No. 9, pp. 1587-1595 (1999).

Maier, J. S., et al, "Possible correlation between blood glucose concentration and the reduced scattering coefficient of tissues in the near infrared," Optics Letters, vol. 19, No. 24, pp. 2062-2064 (Dec. 15, 1994).

March, W., et al, "Optical monitor of glucose," Trans. Am. Soc. Artif. Intern. Organs, vol. 25, pp. 28-31 (1979).

March, W.F., et al, "Noninvasive glucose monitoring of the aqueous humor of the eye: Part II. Animal studies and the scleral lens," Diabetes Care, vol. 5, No. 3, pp. 259-265 (1982).

Mendelson, Y., et al, "Blood glucose measurement by multiple attenuated total reflection and infrared absorption spectroscopy," IEEE Trans. Biomed. Eng., vol. 37, No. 5, pp. 458-465 (1990).

Moreno-Bondi, M.C., et al, "Oxygen optrode for use in a fiber-optic glucose biosensor," Anal. Chem., vol. 62, No. 21, pp. 2377-2380 (1990).

Muller, A., "In vivo measurement of glucose concentration with lasers," Horm. Metab. Res. Suppl., vol. 8, pp. 33-35 (1979).

Narayanaswamy, R., "Current developments in optical biochemical sensors," Biosens. Bioelectron., vol. 6, pp. 467-475 (1991).

Pan, S., et al, "Near-infrared spectroscopic measurement of physiological glucose levels in variable matrices of protein and triglycerides," Anal. Chem., vol. 68, pp. 1124-1135 (1996).

Peterson, J.I., et al, "A miniature fiberoptic pH sensor potentially suitable for glucose measurements," Diabetes Care, vol. 5, No. 3, pp. 272-274 (1982).

Quan, K. M., et al, "Glucose determination by a pulsed photoacoustic technique—an experimental study using a gelatin-based tissue phantom," Phys. Med. Biol., vol. 38, No. 12, pp. 1911-1922 (1993).

Rabinovitch, B., et al, "Noninvasive glucose monitoring of the aqueous humor of the eye: Part I. Measurement of very small optical rotations," Diabetes Care, vol. 5, No. 3, pp. 254-258 (1982).

Robison, M. R., et al, "Noninvasive glucose monitoring in diabetic patients: A preliminary evaluation," Clin. Chem., vol. 38, No. 9, pp. 1618-1622 (1992).

Robinson, R.J., et al, "Glucose-sensitive membrane and infrared absorption spectroscopy for potential use as an implantable glucose sensor," ASAIO J., vol. 38, No. 3, pp. M458-462 (1992).

Rusch, T. L. et al, "Signal Processing Methods for Pulse Oximetry," Comput. Biol. Med., vol. 26, No. 2, pp. 143-159 (1996).

Schimitt, J. M., et al, "Measurement of optical properties of biological tissues by low-coherence reflectometry," Applied Optics, vol. 32, No. 30, pp. 6032-6042 (19930.

Schmitt, J.M., et al, "Speckle in Optical Coherence Tomography," Journal of Biomedical Optics, vol. 4, No. 1, pp. 95-105 (Jan. 1999).

Schmitt, J. M., et al, "Optical Coherence Tomography (OCT): A Review," IEEE Journal of Selected Topics in Quantam Electronics, vol. 5, No. 4, pp. 1205-1214 (Jul./Aug. 1999).

Sevick, E.M., et al, "Near-infrared optical imaging of tissue phantoms with measurement in the change of optical path lengths," Adv. Exp. Med. Biol., vol. 345, pp. 815-823 (1994).

Sodickson, L.A., et al, "Kromoscopic analysis: a possible alternative to spectroscopic analysis for noninvasive measurement of analytes in vivo," Clin. Chem., vol. 40, No. 9, pp. 1838-1844 (1994).

Star, W.M., et al, "Light dosimetry: status and prospects," J. Photochem. Photobiol., vol. 1, No. 2, pp. 149-167 (1987).

Stoddart, S., et al, "Pulse Oximetry: What it is and how to use it," Journal of Neonatal Nursing, pp. 10, 12-14 (Jul. 1997).

Takai, N., et al, "Studies of the development of optical fiber sensors for biochemical analysis," Artif. Organs, vol. 15, No. 2, pp. 86-89 (1991).

Tuchin, V. V., et al, "Light propagation in tissues with controlled optical properties," Journal of Biomed. Opt., vol. 2, No. 4, pp. 401-417 (1997).

Wang, L., et al, "Speckle reduction in laser projection systems by diffractive optical elements," Applied Optics, vol. 37, No. 10, pp. 1770-1775 (Apr. 1, 1998).

Weast, R. C., et al, CRC Handbook of Chemistry and Physics, 70th ed., (CRC Cleveland, Ohio 1989).

Welch, A.J., et al, "Practical models for light distribution in laser-irradiated tissue," Lasers Surg. Med., vol. 6, No. 6, pp. 488-493 (1987).

Wicksted, J. P., et al, "Monitoring of aqueous humor metabolites using Raman spectroscopy," SPIE Proc., vol. 2135, pp. 264-274 (1994).

Zeller, H., et al, "Blood glucose measurement by infrared spectroscopy," J. Artif. Organs, vol. 12, No. 2, pp. 129-135 (1989).

* cited by examiner

METHOD AND APPARATUS FOR TISSUE OXIMETRY

CROSS-REFERENCE TO RELATED APPLICATIONS

This application claims the benefit of U.S. Provisional Application No. 60/485,761 filed by Matthew J. Schurman on Jul. 9, 2003 and entitled *Method and Apparatus For Brain Oximetry*, which application is incorporated herein by reference.

FIELD OF THE INVENTION

The invention pertains to a method and apparatus for measuring the oxygenation of blood-profused biological tissue (tissue oximetry), and more specifically to a method and apparatus for tissue oximetry using low coherence interferometry or optical coherence tomography.

BACKGROUND OF THE INVENTION

Figure 1:
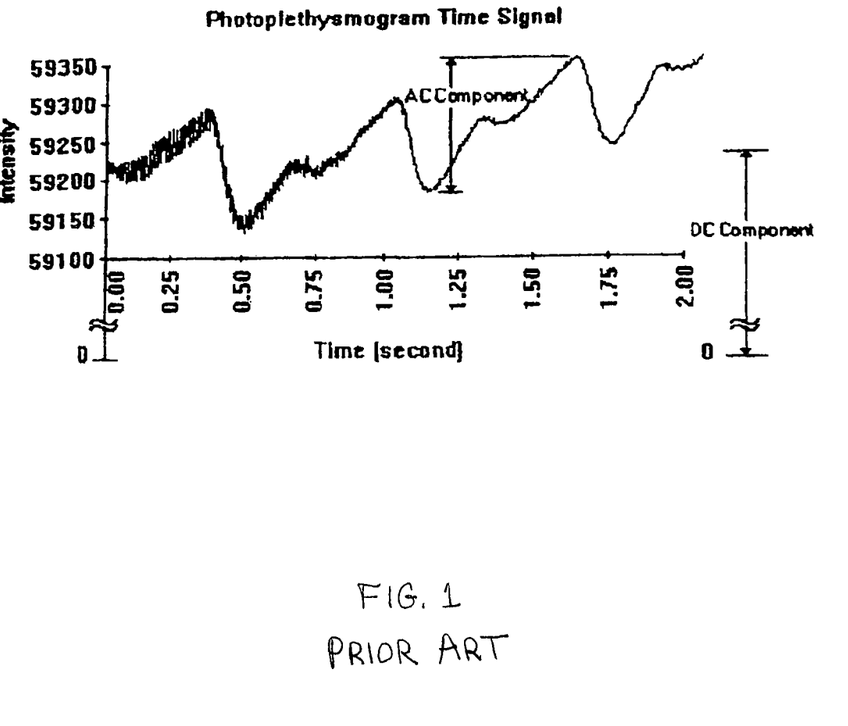
FIG. 1 shows a typical pulse oximetry signal.

Transmission pulse oximetry has long been used in the clinical setting to measure the oxgenation of blood. (See, T. L. Rusch et al, Computers in Biology and Medicine, 26, 143-159, (1996)). In a typical transmission pulse oximetry, two light emitting diodes (LEDs) with peak wavelengths of 660 nm and 940 nm are shone through one side of a finger, and the transmitted light is received via a photodetector positioned on the other side of the finger. The first LED has peak absorption for oxygenated hemoglobin (oxyhemoglobin). The second LED has peak absorption for deoxygenated hemoglobin (reduced hemoglobin or deoxyhemoglobin). As the heart beats, the time varying absorbance signal is recorded. The transmitted light will obey the Beers-Lambert law (Beers law) given by:

$$I_{trans}=I_{in}e^{-DC\alpha},$$

where: $I_{trans}$ is the intensity of the transmitted light, $I_{in}$ is the intensity of initial light, D is the distance the light travels, C is the concentration of the solution, and $\alpha$ is the absorption cross-section of the absorbing species. FIG. 1 graphically illustrates a typical transmission pulse oximetry signal.

In transmission pulse oximetry, hemoglobin is assumed to be composed of two substances: oxyhemoglobin and reduced hemoglobin. Since both species have different absorption cross-sections at the two differing wavelengths, the percentage of each substance in the blood can be calculated.

There are, however, several drawbacks to transmission pulse oximetry. First, it can only be applied to parts of the body where the optical signal can pass from one side of a body part to another side (such as through a finger on an adult, or through a foot on a newborn). Thus, the technique is limited to measuring oxygen saturation at the extremities. In the case of many major surgeries or in the case of trauma, the saturation of blood in the extremities does not reflect the saturation of oxygen at major organs such as the brain. Second, because transmission pulse oximetry relies on transmission through extremities, bright lights can saturate the detector so that the LED signals cannot be read. Third, the technique relies upon the pulsatile signal generated by the beating of the heart. If the blood profusion is low, the pulsatile signal will be small in relation to a baseline DC signal, which can lead to errors in the calculation of the oxygen saturation. Fourth, because the path lengths of the optical signals are not known in pulse transmission oximetry, only the oxygen saturation, and not the actual oxygen level of the blood, can be measured. Accordingly, there is a need for an improved method and apparatus for measuring the oxygenation of blood-profused biological tissue.

SUMMARY OF THE INVENTION

In accordance with the invention, the oxygenation of blood-profused tissue is measured by a method of comprising shining light into the profused tissue and analyzing the light reflected within the tissue. The light is reflected by cell membranes in the tissue and is partially absorbed by hemoglobin in the blood. Since the extent of absorption is sensitive to the extent of hemoglobin oxygenation, measurement and processing of the reflected light provides a measure of the oxygenation of the blood. In one embodiment, the method is applied to measure the oxygenation of blood within the tympanic membrane (ear drum).

Apparatus for measuring the oxygenation of blood-profused tissue comprises one or more light sources to provide light at wavelengths where absorption is sensitive to hemoglobin oxygenation. Light from the sources is directed into the blood-profused tissue, and the light reflected within the tissue is collected, analyzed and measured by an interferometer. A processor responsive to the light measurements then calculates the oxygenation level of the blood-profused tissue. Advantageously, the apparatus uses low coherence light emitting diodes (LEDs) or super luminescent diode light sources (SLEDs) and a low coherence interferometer (LCI).

BRIEF DESCRIPTION OF THE FIGURES

The advantages, nature and various additional features of the invention will appear more fully upon consideration of the illustrative embodiments now to be described in detail in connection with the accompanying drawings. In the drawings.

It is to be understood that the drawings are for the purpose of illustrating the concepts of the invention, and except for the graphs, are not to scale.

DETAILED DESCRIPTION OF THE INVENTION

The invention is directed to devices and methods for measuring the oxygenation of blood-profused biological tissue. More specifically, the invention uses an interferometry technique, such as low coherence interferometry (LCI), optical coherence domain reflectometry (OCDR) or optical coherence tomography, to measure the oxygenation level of blood-profused biological tissue. The invention includes devices and methods of tissue oximetry which illuminate the blood-profused tissue (target tissue) with light, analyze the reflected light to measure hemoglobin absorption, and determine oxygenation from the absorption. In one embodiment, an interferometer is used to measure the reflection of light from an object. An interferometer is an instrument in which light from a source is split into two or more beams which are subsequently reunited after traveling over different paths and display interference.

Any well-known interferometer may be used in the invention. Suitable interferometers for use in the invention include, but are not limited to Michelson interferometers and Mach-Zehnder interferometers. A preferred apparatus uses an interferometer with low coherence light sources to measure reflection of low coherence light from the tissue.

Due to the low optical coherence of the source, the interferogram can only be generated over a small volume whose position in the depth of the object is determined via the position of the reference mirror. Thus a high degree of localization of the measured scattering phenomena can be achieved. For example, for a typical light emitting diode (LED) operating at a 1.3 µm wavelength, a depth resolution of 10 µm is easily achieved in biological tissues. This has been adapted for use in high resolution imaging applications (J. M. Schmitt, IEEE Journal of Quantum Electronics, 5, 1205-1214 (1999)). Typically in biological tissues the scatter of the light occurs at the interface between the cell membrane and the fluid that surrounds the cell (i.e. blood or interstitial fluid).

Figure 2:
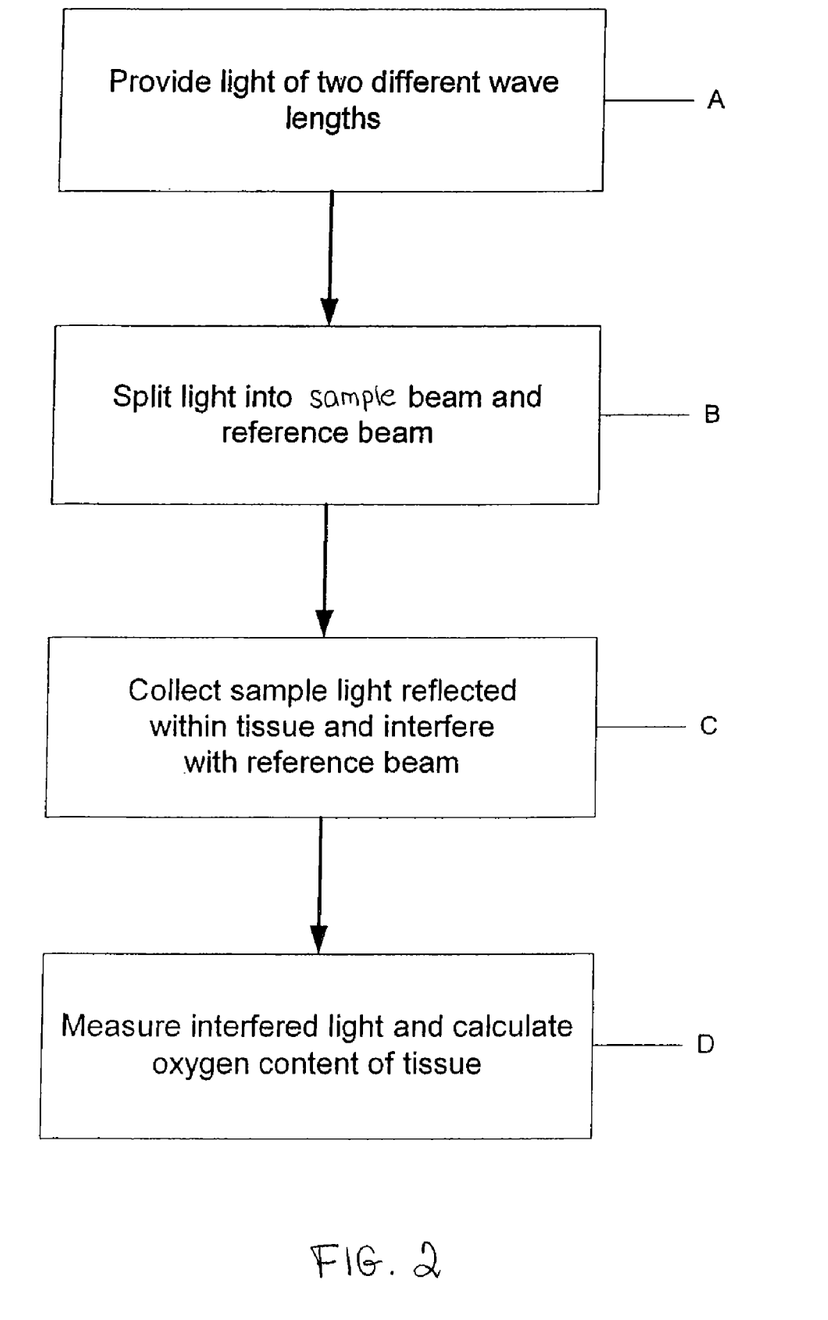
FIG. 2 is a schematic diagram of a method of tissue oximetry in accordance with the invention.

Referring to the drawings, FIG. 2 is a schematic block diagram of an exemplary method of performing tissue oximetry on a human or animal subject. The first step, shown in Block A, is to provide light of at least two different wavelengths. The two different wavelengths should have measurably different absorption and reflectivity from oxygenated and deoxygenated hemoglobin, respectively. Typically the light is provided from two or more sources such as low coherence LEDS at 660 nm and 940 nm. Alternatively it could be provided from a single multiwavelength source or from a single broadband source appropriately notch filtered. The light is advantageously directed in a single beam.

The next step, Block B, is to split the light into a sample beam and a reference beam; directing the sample beam toward the tissue of the subject to illuminate the tissue and directing the reference beam over an adjustable phase path.

The third step of Block C is to collect sample light reflected from within the illuminated tissue and to interfere the reflected light with reference beam light from the adjustable phase path.

The final step (Block D) is to measure the constructively interfered light at the different wavelengths and to process the measurements to provide a measurement of the oxygen content of hemoglobin in the tissue.

Figure 3:
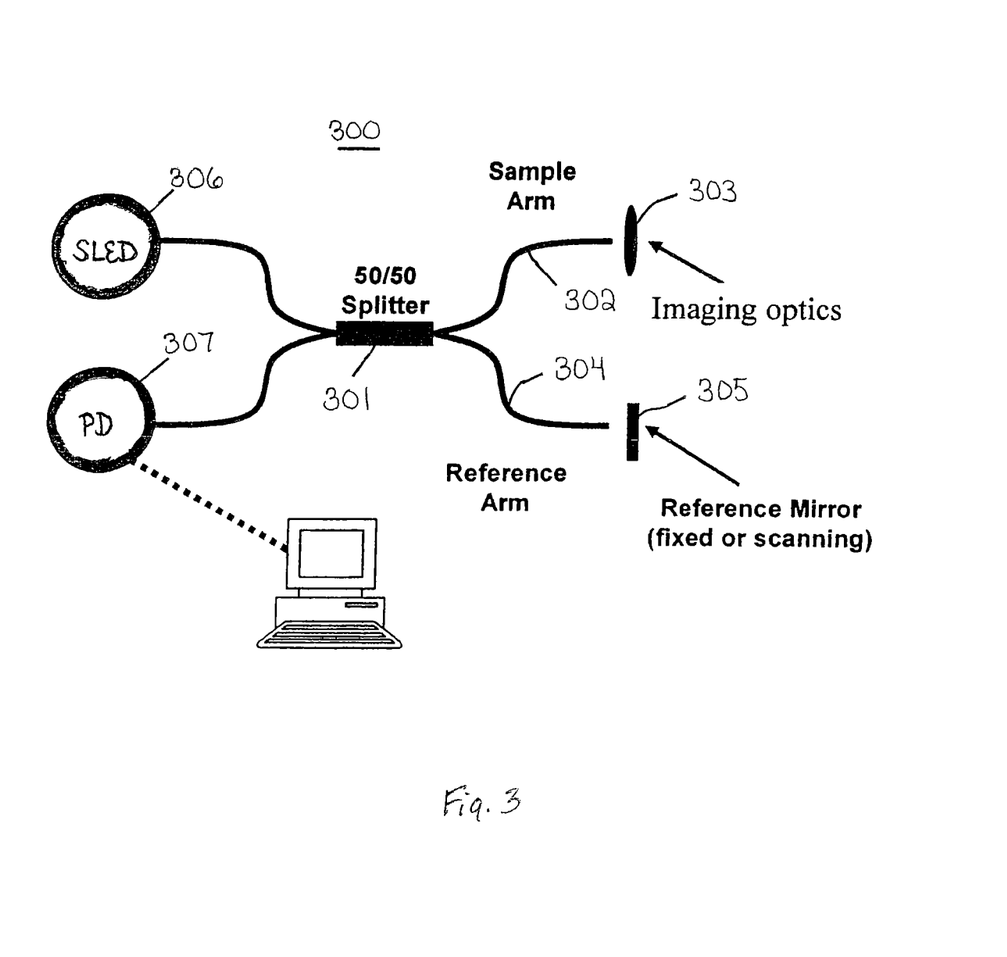
FIG. 3 schematically illustrates apparatus useful for practicing the method of FIG. 2.

FIG. 3 schematically shows exemplary apparatus 300 for practicing the method of FIG. 2. The apparatus 300 comprises a fiber optics-based low coherence interferometer (LCI). A 2×2 fiber optic splitter, for example a 50/50 splitter 301 as shown in FIG. 3, forms the basic interferometer. An optical input from light source 306 is split between a sample arm 302 and a reference arm 304. Reflected signals from arms 302 and 304 interfere and are presented to photodetector 307 for measurement. Preferably, the end of the sample arm 302 can contain imaging optics 303 to tailor the spot size according to the tissue being measured. Advantageously, imaging optics 303 can provide high coupling efficiency between the optical system and the tissue.

The tissue volume with which the light interacts (referred to as the interaction volume) is determined by the spot size of the imaging optics (surface area) and the coherence length of the light (depth). Reference arm 304 of the interferometer determines the phase shift applied to the reference beam and thus which reflected light from the sample will constructively interfere with the shifted reference beam. The reference arm 304 thus determines the depth within the interaction volume from which scattered light will be measured. The arm 304 can have either a fixed or scanning reflector 305 (such as a mirror). This can allow for a fixed sensor depth, adjustable sensor depth, or scan of multiple depths within the tissue. LCI is thus sensitive to the intensity of the reflected light localized in a small volume of tissue. Determination of the depth and interaction volume permits more accurate calculation of both the oxygen concentration and the oxygen saturation of the blood.

Light passing through turbid biological tissue is subject to wavefront distortion that produces coherent noise or "speckle". The use of two different wavelengths helps to reduce the effect of speckle. In addition is it advantageous to rapidly change the interaction region being illuminated as by vibrating the illumination fiber or vibrating a lens directing the illumination beam. Such change reduces the random effect of speckle by spatial averaging.

The effect of speckle is also minimized by appropriate processing of the reflected light. Appropriate processing measures the envelope of the interferogram which contains the intensity information with speckle averaged out (as opposed to measuring absorption from the interferogram itself which would have full speckle noise). Further details concerning such processing are described in "Speckle in Optical Coherence Tomography", *J. Biomed. Optics*, January 1999, pp. 95-105.

The light source 306 can be a light emitting diode (LED) or a super luminescent diode (SLED), both of which are semiconductor based light emitters whose wavelengths can be chosen to give the best contrast in absorption between oxygenated and deoxygenated hemoglobin. Typically these wavelengths are in the red/near infrared (RNIR) region of the spectrum (600 nm to 1600 nm) however, longer and shorter wavelengths can be used for enhanced sensitivity. A unique property of these sources is a wide (>10 nm) spectral bandwidth upon which the low coherence measurement can be based. For the oximetry measurements, two or more light sources are advantageous and can share the same optical paths through the interferometer.

One of the wavelengths can be chosen to have peak absorption for oxygenated hemoglobin e.g. 940 nm; the other wavelength can be chosen to have peak absorption for deoxygenated hemoglobin e.g. 660 nm. Light of the two wavelengths is differently absorbed by the respective hemoglobin species. This differential absorption differentially reduces the intensity of the scattered (reflected) light. Light reflected off the cellular membrane is partially absorbed by the respective hemoglobin species for that wavelength. Where the term "light is reflected from the blood" is used, it is understood to refer to light reflected from the cells in and around the blood vessels and the hemoglobin in the blood absorbs some of the light according to the wavelength and oxygenation of the blood.

Finally a photodetector 307 (such as a photodiode) can be used to measure the interference of the light from both the sample arm 302 and the reference arm 304. One or more photodetectors 307 may be used along with optical fibers (not shown) designed for each of the light sources 306 used in the measurement.

For oximetry, the phase adjusting path of the interferometer may be set to correspond to a fixed depth within tissue comprising blood or a depth profile comprising blood may be scanned. If a depth profile can be scanned, however, the rate of the scan needs to be sufficiently high in order to collect multiple depth scans along a typical heart beat (see FIG. 1). The heart typically beats at 60 beats/minute, however this rate can climb as high as 200 beats/minute. This implies that a minimum of 7 depth scans per second can be needed to satisfy the Nyquist condition for approximating analog signals via digital signal processing. By measuring the intensity of the resulting backscatter signal envelopes, at the different wavelengths, the concentration of oxygenated hemoglobin can be determined utilizing the same well known algorithms that are used in standard transmission pulse oximetry.

Figure 4:
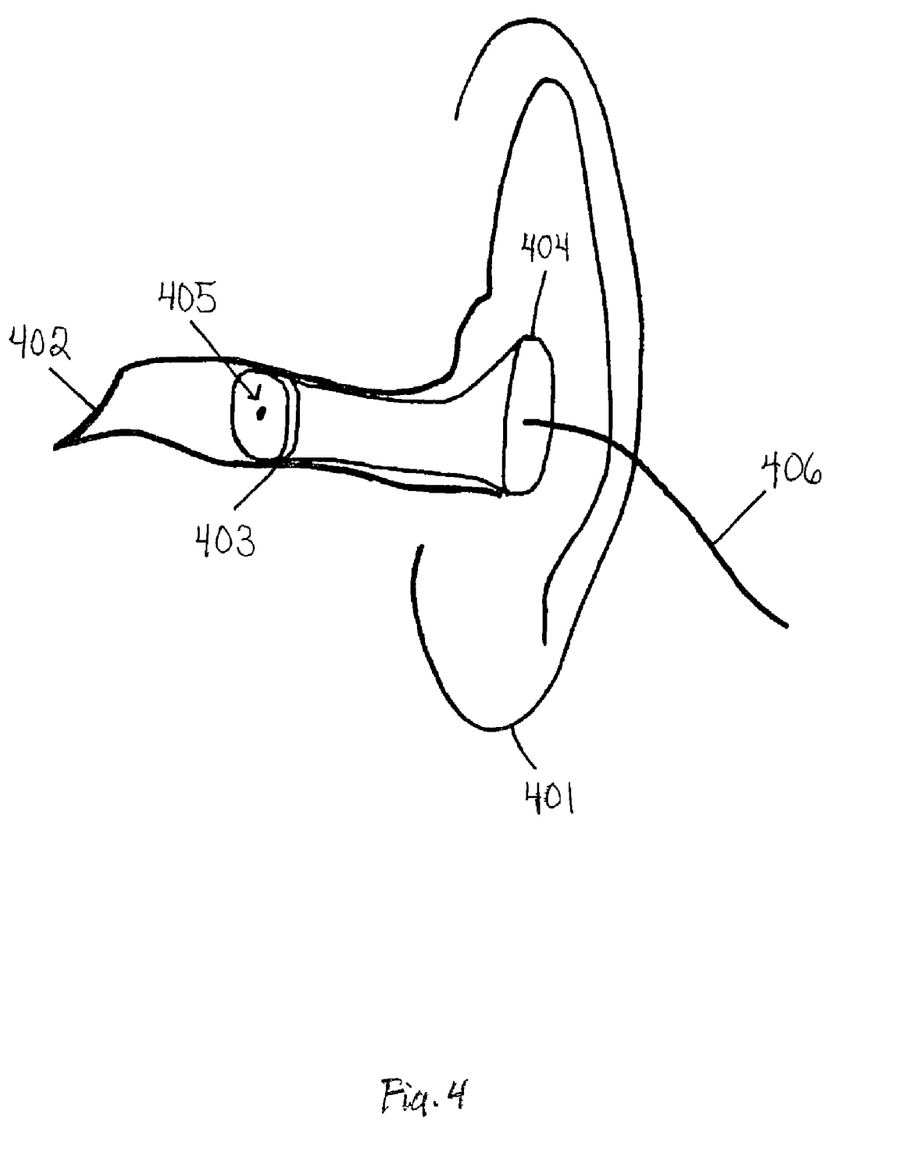
FIG. 4 illustrates one embodiment of the FIG. 3 apparatus where a probe is inserted in an ear for providing a measure of brain oximetry.

As one exemplary application, it is notoriously difficult to measure the oxygenation of blood feeding the brain. The apparatus of FIG. 3 can make such challenging measurements. There should be substantial equivalence between the oxygenation of tympanic blood with the oxygenation of the blood that feeds the brain. The invention can measure the oxygenation of tympanic membrane blood, to determine the oxygenation of blood in the brain (brain oximetry). In the case of brain oximetry, as shown in FIG. 4, the optics head 405 can be placed in the ear 401 near the tympanic membrane 402 (ear drum). This can be achieved by threading the optics head 405 through an earplug 404 that can then be placed in the ear canal 403 in proximity to the tympanic membrane. Optical fiber 406 connects the optics head to the splitter. The reference arm delay can be adjusted to get the strongest absorption profile so that the surface reflections are being collected from the tympanic membrane by probe 405 (comprising the sample arm). The fixed depth, or depth scan, can then be set from this base line.

It can now be seen that the invention includes a tissue oximetry method comprising the steps of illuminating tissue containing blood with light, analyzing the reflected light to measure hemoglobin absorption, and determining oxygenation from the absorption. In an advantageous embodiment, light reflected from the tympanic membrane is interfered with reference light and the interfered reflected light is measured and processed to provide a measure of the oxygenation of the blood flowing into the brain. Preferably the light reflected within the blood is measured by low coherence interferometry.

In a preferred embodiment, the method comprises the steps of providing a low coherence interferometer having a sample arm, a reference arm, a reference arm reflector and one or more detectors. Light of first and second wavelengths is provided for illuminating both the sample arm and the reference arm reflector. The sample arm is used as a probe to illuminate blood-profused tissue and to sample the light reflected from the tissue. The light reflected from the tympanic membrane is interfered with the light from the reference arm reflector to select the light reflected within the blood, and the constructively interfered light is detected and processed to yield a measurement of tissue oxygenation. The processing can be done by a computer. Also, the reference arm can be phase adjusted for the strongest absorption profile.

In another embodiment, an apparatus for tissue oximetry of an animal or human subject comprises one or more sources of light providing light at two different wavelengths whose absorption in hemoglobin is sensitive to hemoglobin oxygenation. Light guides direct a beam of light from the sources onto blood-profused tissue of the subject and also serve to receive light reflected from within the tissue. An interferometer interferes the reflected light with a phase adjusted sample of the beam, the phase adjustment chosen to select by constructive interference, the light reflected from blood within the tissue. One or more photodetectors measure the constructively interfered light; and a processor (computer or microprocessor) determines the oxygenation of the blood from the measurements.

The apparatus can comprise a low coherence interferometer. The interferometer can comprise a beam splitter for splitting the light into a sample beam and a reference beam, light guides for directing a beam of light from the sources onto the tissue and for receiving light reflected from within the tissue, and light guides for directing a sample of the light from the sources to a reference arm and reference reflector.

Further, the splitter can be a 2×2 optical splitter. The reflector can be a mirror. And, the reference arm delay can be phase adjustable. The photodetector can comprise a photodiode. And, the light source can be a light emitting diode (LED), or a super luminescent diode (SLED).

It is understood that the above-described embodiments are illustrative of only a few of the many possible specific embodiments, which can represent applications of the invention. Numerous and varied other arrangements can be made by those skilled in the art without departing from the spirit and scope of the invention.

I claim:

1. A method of tissue oximetry on a human or animal subject comprising the steps of:
providing light of at least two different wavelengths, the light of the two wavelengths having different absorption and different reflectivity from oxygenated hemoglobin and deoxygenated hemoglobin, respectively;
splitting the light into a sample beam and a reference beam;
illuminating tissue of the subject with the sample beam, the sample beam being moved to at least two spatially distinct illuminated interaction regions to reduce a speckle effect;
collecting light reflected from within the illuminated tissue;
interfering the reflected light with reference light from the reference beam, the reference light being adjusted in phase to constructively interfere with the reflected light; and
measuring the interfered light and processing the measurements to determine the oxygen content of hemoglobin in the tissue.

2. The method of claim 1 wherein the light is provided by one or more low coherence sources.

3. A method of tissue oximetry on a subject comprising the steps of:
providing a low coherence interferometer comprising a sample arm, a reference arm, a reference arm reflector and one or more detectors;
providing a light source for illuminating tissue of the subject and the reference arm;
positioning the sample arm, to sample the light reflected from within the tissue, the sample arm configured to reduce a speckle effect by averaging reflected light from at least two spatially distinct interaction regions;
interfering light reflected from the tissue and light from the reference arm reflector, the light from the reference arm reflector adjusted to constructively interfere with the light reflected from the tissue; and
detecting and processing the interfered light to yield a measurement of blood oxygenation.

4. The method of claim 3 wherein processing comprises processing by computer or microprocessor.

5. The method of claim 3 further comprising the step of increasing the absorption profile by adjusting the pathlength of the reference arm.

6. An apparatus for tissue oximetry of an animal or human subject comprising:
one or more sources of light to provide light at two different wavelengths that respectively absorb and reflect differently from oxygenated hemoglobin;
a first light path to direct a beam of light from the sources onto the tissue of the subject and to receive reflected light from the tissue, the first light path configured to reduce a speckle effect by averaging reflected light from at least two spatially distinct interaction regions;
a second light path to direct a beam of reference light from the one or more sources to a phase adjuster;
an interferometer to interfere the reflected light with the phase adjusted reference light, the phase adjustment of the reference light chosen to select by constructive interference, the light reflected from tissue comprising blood;
one or more photodetectors to measure the interfered light; and
a processor to determine the oxygenation of the blood from the measurements.

7. The apparatus according to claim 6 wherein the sources are low coherence sources and the interferometer comprises a low coherence interferometer.

8. The apparatus according to claim 6 wherein the interferometer comprises:
a beam splitter to split the light into a sample beam and a reference beam, and
a reference light path to direct the reference beam from the phase adjuster into interference with the reflected light from the tissue,
wherein the first light path comprises at least one light guide for directing light from the one or more sources onto the tissue of the subject and to receive light reflected from within the tissue.

9. The apparatus of claim 6 wherein the beam splitter comprises a 2×2 optical splitter.

10. The apparatus of claim 6 wherein the second light path comprises a reflector to adjust the path length.

11. The apparatus of claim 6, wherein the one or more photodetectors comprise a photodiode.

12. The apparatus of claim 6 wherein at least one light source comprises a light emitting diode (LED) or a superluminescent diode (SLED).

* * * * *